(12) United States Patent
Lee et al.

(10) Patent No.: US 8,722,409 B2
(45) Date of Patent: May 13, 2014

(54) COFILIN KNOCKDOWN HOST CELLS AND USES THEREOF

(75) Inventors: Kelvin H. Lee, Newark, DE (US); Stephanie Hammond, Newark, DE (US)

(73) Assignee: University of Delaware, Newark, DE (US)

( * ) Notice: Subject to any disclaimer, the term of this patent is extended or adjusted under 35 U.S.C. 154(b) by 227 days.

(21) Appl. No.: 13/294,759

(22) Filed: Nov. 11, 2011

(65) Prior Publication Data
US 2012/0129218 A1 May 24, 2012

Related U.S. Application Data

(60) Provisional application No. 61/412,598, filed on Nov. 11, 2010, provisional application No. 61/469,395, filed on Mar. 30, 2011, provisional application No. 61/530,561, filed on Sep. 2, 2011, provisional application No. 61/532,366, filed on Sep. 8, 2011.

(51) Int. Cl.
| C12N 15/00 | (2006.01) |
| C12N 5/00  | (2006.01) |
| C12N 5/02  | (2006.01) |
| C12N 5/07  | (2010.01) |
| C12N 5/10  | (2006.01) |
| C12Q 1/68  | (2006.01) |
| C07H 21/02 | (2006.01) |
| C07H 21/04 | (2006.01) |
| C12N 15/11 | (2006.01) |

(52) U.S. Cl.
USPC ............ 435/455; 435/6.1; 435/325; 435/358; 435/359; 536/23.1; 536/24.5; 514/44 A

(58) Field of Classification Search
None
See application file for complete search history.

(56) References Cited

U.S. PATENT DOCUMENTS

2012/0009202 A1* 1/2012 Coombs et al. ............ 424/159.1

OTHER PUBLICATIONS

Ahn WS, et al. (2008). Effect of culture temperature on erythropoietin production and glycosylation in a perfusion culture of recombinant CHO cells. Biotechnol Bioeng. 101(6):1234-44.
Alete DE, et al. 2005. Proteomic analysis of enriched microsomal fractions from GS-NS0 murine myeloma cells with varying secreted recombinant monoclonal antibody productivities. Proteomics 5(18):4689-704.
Allen MJ, et al. (2008). Identification of novel small molecule enhancers of protein production by cultured mammalian cells. Biotechnol Bioeng. 100(6):1193-204.
Andersen DC and Krummen L (2002). Recombinant protein expression for therapeutic applications. Current Opinion in Biotechnology, 13: 117-123.

Andrianantoandro E and Pollard TD. (2006). Mechanism of actin filament turnover by severing and nucleation at different concentrations of ADF/cofilin. Mol Cell 24(1):13-23.
Bender BW, et al. (2010). ADF/n-cofilin-dependent actin turnover determines platelet formation and sizing. Blood 116(10):1767-75.
Bernstein BW and Bamburg JR. (2010). ADF/Cofilin: a functional node in cell biology. Trends Cell Biol 20:187-95.
Beuger V, et al. (2009). Short-hairpin-RNA-mediated silencing of fucosyltransferase 8 in Chinese-hamster ovary cells for the production of antibodies with enhanced antibody immune effector function. Biotechnology and Applied Biochemistry 53, 31-37.
Carlage T, et al. (2009). Proteomic profiling of a high-producing Chinese hamster ovary cell culture. Anal Chem 81(17):7357-62.
Chan AY, et al. (2000). Role of cofilin in epidermal growth factor-stimulated actin polymerization and lamellipod protrusion. J Cell Biol 148(3):531-42.
Chua BT, et al. (2003). Mitochondrial translocation of cofilin is an early step in apoptosis induction. Nat Cell Biol 5(12):1083-9.
Chung JY, et al. (2004). Effect of doxycycline-regulated calnexin and calreticulin expression on specific thrombopoietin productivity of recombinant Chinese hamster ovary cells. Biotechnol Bioeng. 85(5):539-46.
Collen D and Lijnen HR. (2004). Tissue-type plasminogen activator: a historical perspective and personal account. J Thromb Haemost. 2(4):541-6.
Cost GJ, et al. BAK and BAX deletion using zinc-finger nucleases yields apoptosis-resistant CHO cells. Biotechnology and Bioengineering (2010) 105, 330-340.
Dawe HR, et al. (2003). ADF/cofilin controls cell polarity during fibroblast migration. Curr Biol 13(3):252-7.
DesMarais V et al. (2005). Cofilin takes the lead. Journal of Cell Biology, 118: 19-26.
Dinnis DM and James DC. (2005). Engineering mammalian cell factories for improved recombinant monoclonal antibody production: lessons from nature? Biotechnol Bioeng 91(2):180-9.
Elbashir SM, et al. Duplexes of 21-nucleotide RNAs mediate RNA interference in cultured mammalian cells. Nature (2001) 411, 494-498.
Elbashir SM, et al. (2002). Analysis of gene function in somatic mammalian cells using small interfering RNAs. Methods. 26(2):199-213.
Grzanka D, et al. (2010). Doxorubicin-induced F-actin reorganization in cofilin-1 (nonmuscle) down-regulated Cho AA8 cells. Folia Histochem Cytobiol 48(3):377-86.
Hammond S, et al. (2010). Enhancing Recombinant Protein Production in CHO Cells Using Genomic Tools and Cofilin siRNA, Cell Culture Engineering XII conference, Banff, Alberta, Canada.

(Continued)

*Primary Examiner* — Dana Shin
(74) *Attorney, Agent, or Firm* — RatnerPrestia

(57) ABSTRACT

The present invention relates to a host cell comprising a cofilin-specific small interfering RNA (siRNA) sequence. The host cell may further comprise a nucleic acid encoding a recombinant protein. The present invention also relates to a method for producing a recombinant protein by the host cell comprising a cofilin-specific small interfering RNA (siRNA) sequence.

15 Claims, 5 Drawing Sheets
(1 of 5 Drawing Sheet(s) Filed in Color)

(56) References Cited

OTHER PUBLICATIONS

Hammond S, et al. (2011). Genomic sequencing and analysis of a Chinese Hamster ovary cell line using Illumina sequencing technology. BMC Genomics 12:67.

Han L, et al. (2007). Direct stimulation of receptor-controlled phospholipase D1 by phospho-cofilin. Embo J 26(19):4189-202.

Hayduk EJ and Lee KH. (2005). Cytochalasin D can improve heterologous protein productivity in adherent Chinese hamster ovary cells. Biotechnol Bioeng 90(3):354-64.

Hong WW and Wu SC. A novel RNA silencing vector to improve antigen expression and stability in Chinese hamster ovary cells. Vaccine (2007) 25, 4103-4111.

Hotulainen P, et al. (2005). Actin-depolymerizing factor and cofilin-1 play overlapping roles in promoting rapid F-actin depolymerization in mammalian nonmuscle cells. Mol Biol Cell 16(2):649-64.

Ichetovkin I, et al. (2002). Cofilin produces newly polymerized actin filaments that are preferred for dendritic nucleation by the Arp2/3 complex. Curr Biol 12(1):79-84.

Kandasamy MK, et al. (2010). Differential sublocalization of actin variants within the nucleus. Cytoskeleton 67(11):729-43.

Kantardjieff A, et al. (2010). Transcriptome and proteome analysis of Chinese hamster ovary cells under low temperature and butyrate treatment. J Biotechnol 145(2):143-59.

Kim SH and Lee GM. Down-regulation of lactate dehydrogenase-A by siRNAs for reduced lactic acid formation of Chinese hamster ovary cells producing thrombopoietin. Appl Microbiol Biotechnol. Feb. 2007; 74(1):152-9. Epub Nov. 4, 2006.

Kim TK, et al. (2000). Osmoprotective effect of glycine betaine on thrombopoietin production in hyperosmotic Chinese hamster ovary cell culture: clonal variations. Biotechnol Prog. 16(5):775-81.

Klamt F, et al. (2009). Oxidant-induced apoptosis is mediated by oxidation of the actin-regulatory protein cofilin. Nat Cell Biol 11(10):1241-6.

Kumar N, et al. (2008). Differential protein expression following low temperature culture of suspension CHO-K1 cells. BMC Biotechnol 8:42.

Kuystermans D, et al. (2010). A proteomic study of cMyc improvement of CHO culture. BMC Biotechnol 10:25.

Lee KH, et al. (2000). Cofilin: a missing link between T cell co-stimulation and rearrangement of the actin cytoskeleton. Eur J Immunol 30(3):892-9.

Lee SK and Lee GM. (2003). Development of apoptosis-resistant dihydrofolate reductase-deficient Chinese hamster ovary cell line. Biotechnol Bioeng. 82(7):872-6.

Lim SF, et al. RNAi suppression of Bax and Bak enhances viability in fed-batch cultures of CHO cells. Metabolic Engineering (2006) 8, 509-522.

Mahmoudifar N and Doran PM. (2010). Extent of cell differentiation and capacity for cartilage synthesis in human adult adipose-derived stem cells: comparison with fetal chondrocytes. Biotechnol Bioeng. 107(2):393-401.

Meleady P, et al. (2008). Proteomic profiling of CHO cells with enhanced rhBMP-2 productivity following co-expression of PACEsol. Proteomics 8(13):2611-24.

Mimura Y, et al. (2001). Butyrate increases production of human chimeric IgG in CHO-K1 cells whilst maintaining function and glycoform profile. Immunol Methods. 247(1-2):205-16.

Mohan C, et al. (2008). Assessment of cell engineering strategies for improved therapeutic protein production in CHO cells. Biotechnol J. 3(5):624-30.

Mori K, et al. (2004). Engineering Chinese hamster ovary cells to maximize effector function of produced antibodies using FUT8 siRNA. Biotechnol Bioeng 88(7):901-8.

Ng SK, et al. (2007). Application of destabilizing sequences on selection marker for improved recombinant protein productivity in CHO-DG44. Metab Eng. 9(3):304-16. Epub Feb. 14, 2007.

Ngantung FA, et al. (2006). RNA interference of sialidase improves glycoprotein sialic acid content consistency. Biotechnol Bioeng 95(1):106-19.

Nishita M, et al. (2005). Spatial and temporal regulation of cofilin activity by LIM kinase and Slingshot is critical for directional cell migration. J Cell Biol 171(2):349-59.

Pascoe DE, et al. (2007). Proteome analysis of antibody-producing CHO cell lines with different metabolic profiles. Biotechnol Bioeng 98(2):391-410.

Rasmussen B, et al. (1998). Isolation, characterization and recombinant protein expression in Veggie-CHO: A serum-free CHO host cell line. Cytotechnology 28(1-3):31-42.

Rodriguez J, et al. (2005). Enhanced production of monomeric interferon-beta by CHO cells through the control of culture conditions. Biotechnol Prog. 21(1):22-30.

Running Deer J. And Allison DS. (2004). High-level expression of proteins in mammalian cells using transcription regulatory sequences from the Chinese hamster EF-1alpha gene. Biotechnol Prog. 20(3):880-9.

Santiago Y, et al. (2008). Targeted gene knockout in mammalian cells by using engineered zinc-finger nucleases. Proc Natl Acad Sci USA. 105(15):5809-14. Epub Mar. 21, 2008.

Sidani M, et al. (2007). Cofilin determines the migration behavior and turning frequency of metastatic cancer cells. J Cell Biol 179(4):777-91.

Smales CM, et al. (2004). Comparative proteomic analysis of GS-NS0 murine myeloma cell lines with varying recombinant monoclonal antibody production rate. Biotechnol Bioeng 88(4):474-88.

Sung YH, et al. (2007). Influence of co-down-regulation of caspase-3 and caspase-7 by siRNAs on sodium butyrate-induced apoptotic cell death of Chinese hamster ovary cells producing thrombopoietin. Metab Eng. 9(5-6):452-64. Epub Aug. 25, 2007.

Takahashi Y et al. (2009). Nonviral vector-mediated RNA interference: Its gene silencing characteristics and important factors to achieve RNAi-based gene therapy. Advanced Drug Delivery Reviews, 61: 760-766.

Tan HK, et al. (2008). Overexpression of cold-inducible RNA-binding protein increases interferon-gamma production in Chinese-hamster ovary cells. Biotechnol Appl Biochem. 49(Pt 4):247-57.

Tigges M and Fussenegger M. (2006). Xbp1-based engineering of secretory capacity enhances the productivity of Chinese hamster ovary cells. Metab Eng. 8(3):264-72.

Tsai CH, et al. (2009). Regulated expression of cofilin and the consequent regulation of p27(kip1) are essential for G(1) phase progression. Cell Cycle 8(15):2365-74.

Vartiainen MK, et al. (2002). The three mouse actin-depolymerizing factor/cofilins evolved to fulfill cell-type-specific requirements for actin dynamics. Mol Biol Cell 13(1):183-94.

von Blume J, et al. (2009). Actin remodeling by ADF/cofilin is required for cargo sorting at the trans-Golgi network. J Cell Biol 187(7):1055-69.

Wu SC, et al. (2008). Short hairpin RNA targeted to dihydrofolate reductase enhances the immunoglobulin G expression in gene-amplified stable Chinese hamster ovary cells. Vaccine. 26(38):4969-74. Epub Jul. 9, 2008.

Wu SC. (2009). RNA interference technology to improve recombinant protein production in Chinese hamster ovary cells. Biotechnol Adv. 27(4):417-22. Epub Mar. 14, 2009.

Wurm FM. (2004). Production of recombinant protein therapeutics in cultivated mammalian cells. Nat Biotechnol. 22(11):1393-8.

Xing J, et al. (2009). Altering Recombinant Protein Production Using RNA Interference, University of Delaware Summer Undergraduate Research Symposium, Newark, DE, USA.

Zhang M, et al. (2010). Enhancing glycoprotein sialylation by targeted gene silencing in mammalian cells. Biotechnol Bioeng 105(6):1094-105.

\* cited by examiner

COFILIN KNOCKDOWN HOST CELLS AND USES THEREOF

CROSS-REFERENCE TO RELATED APPLICATION

This application claims the benefit of U.S. Provisional Application Nos. 61/412,598, filed Nov. 11, 2010, 61/469,395, filed Mar. 30, 2011, 61/530,561, filed Sep. 2, 2011, and 61/532,366, filed Sep. 8, 2011, the contents of each of which are incorporated herein by reference in their entireties for all purposes.

FIELD OF THE INVENTION

The invention relates generally to host cells comprising a cofilin-specific small interfering RNA (siRNA) sequence to knock down or reduce production of cofilin protein in the host cells, and uses of the host cells for producing recombinant proteins.

BACKGROUND OF THE INVENTION

Chinese hamster ovary (CHO) cells are the most commonly used mammalian cell line for production of biopharmaceutical proteins. Generation of hyperproductive CHO cell lines likely involves the coordinated re-programming of multiple metabolic, secretory, and signaling pathways. To enhance recombinant protein production, such as biopharmaceuticals, in mammalian host cell lines, several strategies are currently employed including optimization of expression vectors and gene amplification methods, media composition and cell culture processes, and cell line engineering to alter apoptosis, growth rates, and metabolic pathways.

Gene silencing using RNA interference (RNAi) technology is a recent approach to alter signaling and metabolic pathways in CHO cells. CHO cell lines with improved viability, enhanced recombinant protein expression and stability, and increased efficacy of monoclonal antibodies were recently generated using RNAi technology. The recent development of genome-scale technologies permits direct cell engineering by manipulating single genes that play important roles in metabolic or regulatory pathways to generate high-producing cell lines. For example, during methotrexate (MTX)-amplification of CHO cells expressing human secreted alkaline phosphatase (SEAP), expression of the actin binding protein cofilin was found to decrease nearly 10-fold as specific SEAP productivity increased.

There remains a need for host cells, especially CHO cells, to be engineered to produce recombinant biopharmaceutical proteins at high levels.

SUMMARY OF THE INVENTION

The present invention relates to cofilin knockdown host cells. In particular, the host cells comprise a cofilin-specific small interfering RNA (siRNA) sequence, and are used for producing recombinant proteins.

According to one aspect of the present invention, a host cell comprising a cofilin-specific small interfering RNA (siRNA) sequence is provided. The host cell produces less cofilin protein than a control cell, for example, by at least 10%.

The cofilin-specific siRNA sequence may comprise SEQ ID NO: 1 or SEQ ID NO: 2. The host cell may express the cofilin-specific siRNA sequence transiently or stably.

The host cell may be a mammalian cell, and may be selected from the group consisting of 3T3, CHO, BHK, HeLa, NS0, and HepG2 cells and derivatives of these cells. Preferably, the host cell is a CHO cell. The host cell may be adherent or in suspension, preferably in suspension.

The host cell may further comprise a nucleic acid sequence encoding a recombinant protein. The host cell may produce the recombinant protein. Preferably, the host cell produces more recombinant protein than a control cell, for example, by at least 40%. The host cell may have been transfected with a vector comprising the nucleic acid sequence encoding the recombinant protein. The recombinant protein may be selected from the group consisting of monoclonal antibodies (e.g., anti-EGFR mAb, anti-VEGF mAb, Factor VIII, anti-IgE mAb, anti-CD11a mAb, interferon-(, anti-TNFα mAb, anti-CD52 mAb, anti-HER2 mAb, and anti-CD20 mAb), human secreted alkaline phosphatase (SEAP), tissue plasminogen activator (tPA), α-glucosidase, laronidase, Ig-CTLA4 fusion, N-acetylgalactosamine-4-sulfatase, luteinizing hormone, erythropoietin, TNFα receptor fusion, Factor IX, follicle stimulating hormone, β-glucocerebrosidase, and deoxyribonuclease I. Preferably, the recombinant protein is human secreted alkaline phosphatase (SEAP) or tissue plasminogen activator (tPA).

According to another aspect of the present invention, a method of producing a recombinant protein by a host cell comprising a cofilin-specific small interfering RNA (siRNA) sequence and a nucleic acid sequence encoding the recombinant protein is provided. The method comprises growing the host cell in a culture medium, wherein the host cell produces the recombinant protein. The host cell produces less cofilin protein than a control cell, for example, by at least 10%. The method may further comprise isolating the recombinant protein from the host cell.

In the method of the present invention, the cofilin-specific siRNA sequence may comprise SEQ ID NO: 1 or SEQ ID NO: 2. The host cell may express the cofilin-specific siRNA sequence transiently or stably. The host cell may be a mammalian cell, and may be selected from the group consisting of 3T3, CHO, BHK, HeLa, NS0, and HepG2 cells and derivatives of these cells. Preferably, the host cell is a CHO cell. The host cell may be adherent or in suspension, preferably in suspension.

In the method of the present invention, the host cell may produce the recombinant protein at least 40% more than the control cell. The host cell may have been transfected with a vector comprising the nucleic acid sequence encoding the recombinant protein. The recombinant protein may be selected from the group consisting of monoclonal antibodies (e.g., anti-EGFR mAb, anti-VEGF mAb, Factor VIII, anti-IgE mAb, anti-CD11a mAb, interferon-β, anti-TNFα mAb, anti-CD52 mAb, anti-HER2 mAb, and anti-CD20 mAb), human secreted alkaline phosphatase (SEAP), tissue plasminogen activator (tPA), α-glucosidase, laronidase, Ig-CTLA4 fusion, N-acetylgalactosamine-4-sulfatase, luteinizing hormone, erythropoietin, TNFα receptor fusion, Factor IX, follicle stimulating hormone, β-glucocerebrosidase, and deoxyribonuclease I. Preferably, the recombinant protein is human secreted alkaline phosphatase (SEAP) or tissue plasminogen activator (tPA).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
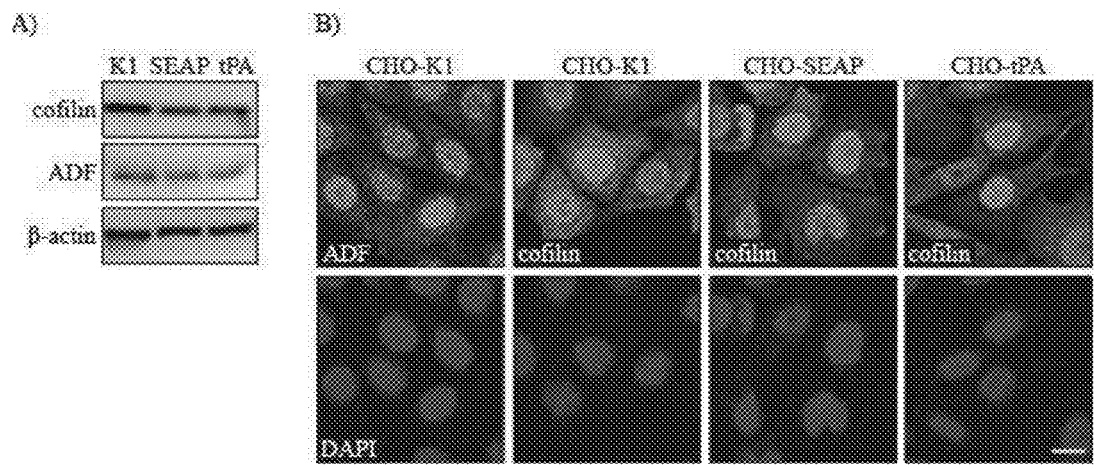
FIG. 1 shows expression and localization of ADF/cofilin in CHO cell lines: (A) expression of ADF/cofilin in CHO cell lines analyzed by western blotting, in which β-actin was used as a loading control, and (B) subcellular distribution of ADF/cofilin proteins in CHO cells. CHO-K1 cells were labeled with anti-ADF and anti-cofilin (upper panels). CHO-SEAP and CHO-tPA cells were labeled with anti-cofilin (upper panels). Nuclei were counterstained with DAPI (bottom panels). The scale bar represents 10 μM.

The present invention is based on the discovery that selectively reducing the production level of an actin cytoskeletal regulatory protein, cofilin 1, by RNAi enhances specific productivity of recombinant proteins in CHO cells. The present invention relates to a direct cell engineering approach using RNAi to selectively reduce the production level of a cofilin protein in a host cell. Recombinant protein productivity is enhanced by using RNAi to destabilize the actin cytoskeleton in the host cell.

The terms "protein" and "polypeptide" are used herein interchangeably, and refer to a polymer of amino acid residues with no limitation with respect to the minimum length of the polymer. Preferably, the protein or polypeptide has at least 20 amino acids. The definition includes both full-length proteins and fragments thereof, as well as modifications thereof (e.g., glycosylation, phosphorylation, deletions, additions and substitutions).

The term "polynucleotide" used herein refers to a polymer of nucleotide residues with no limitation with respect to the minimum length of the polymer. Preferably, the polynucleotide has at least 60 nucleotides. The polynucleotide may be a DNA, cDNA or RNA molecule.

The term "variant" of a protein or polynucleotide used herein refers to a polypeptide or polynucleotide having an amino acid or nucleic acid sequence that is the same as the amino acid or nucleic acid sequence of the protein or polynucleotide except having at least one amino acid or nucleic acid modified, for example, deleted, inserted, or replaced, respectively. A variant of a protein or polynucleotide may have an amino acid or nucleic acid sequence at least about 80%, 90%, 95%, or 99%, preferably at least about 90%, more preferably at least about 95%, identical to the amino acid sequence or nucleic acid of the protein or polynucleotide.

Cofilin 1, also known as CFL1, is a member of the actin depolymerizing factor (ADF)/cofilin family, which are ubiquitously expressed and highly conserved actin binding proteins. Three isoforms of cofilin are differentially expressed in mammals: cofilin 2 in muscle cells, cofilin 1 in non-muscle cells, and ADF in epithelial and endothelial cells. While cofilin 1 and ADF are co-expressed in cultured non-muscle mammalian cell lines, cofilin 1 is the more abundant isoform.

The term "cofilin protein" used herein refers to a full length cofilin protein, or a functional fragment or variant thereof. A cofilin protein may be cofilin 1, cofilin 2, or ADF. Cofilin protein sequences and gene sequences in various species (e.g., human, mouse, rat and Chinese hamster) are known in the art. For example, actual or predicted full-length mRNA sequences of human, mouse, rat and Chinese hamster cofilin 1 can be found in the GenBank database Accession Nos. NM_005507.2, NM_007687, NM_017147, and XM_003512921.1 and XM_003502017.1, respectively. A functional fragment of a cofilin protein is a cofilin fragment capable of binding to and altering the actin filament structure. For example, a functional cofilin fragment may include amino acid residues 4 to 153 of the human cofilin 1 protein.

The present invention provides a host cell comprising a cofilin-specific small interfering RNA (siRNA) sequence. The host cell produces less cofilin protein than a control cell. A control cell is the same as the host cell except lacking the cofilin-specific siRNA sequence.

The host cell may be a mammalian cell, preferably a mammalian cell suitable for producing a recombinant protein. The host cell may be selected from the group consisting of 3T3, CHO, BHK, HeLa, HepG2 and NS0 cells, and derivatives of these cells. Preferably, the host cell is a CHO cell. The host cell may be adherent or in suspension, preferably in suspension.

The term "cofilin-specific small interfering RNA (siRNA) sequence" as used herein refers to a nucleic acid sequence (RNA or DNA) capable of interfering with the expression of a cofilin gene and causing knockdown of the corresponding cofilin protein in a host cell comprising the nucleic acid sequence when compared with that in a control cell. The term "knockdown" of a protein used herein means reduced production of the protein. Conventional RNAi design and construction techniques may be used to make a cofilin-specific siRNA sequence complementary with a segment of the cofilin mRNA sequence in a host cell. Where the cofilin mRNA sequence is not known in a host cell, a cofilin cDNA may be isolated from the host cell using conventional techniques known in the art. For example, a cofilin cDNA has been isolated from CHO-K1 cells and sequenced to define target regions for gene silencing based on previously published siRNA design guidelines (Elbashir et al., *Methods* (2002) 26:199-213). Various sequence segments, preferably conserved regions within the cofilin cDNA sequence among different species may be selected. For example, the cofilin-specific siRNA sequence may comprise a sequence of 5'-CUAACUGCUACGAGGAGGU-3'(S1) (SEQ ID NO:1) or 5'-GAAGAACAUCAUCCUGGAG-3' (S2) (SEQ ID NO:2), targeting a cofilin 1 mRNA segment sequence corresponding to CAAACTGCTACGAGGAGGT (SEQ ID NO: 3) or GAAGAACATCATCCTGGAG (SEQ ID NO: 4), respectively. siRNA duplexes may be synthesized, and screened for silencing efficiency in, for example, CHO-SEAP cells, which are CHO cells engineered to express human secreted alkaline phosphatase (SEAP), a model recombinant protein.

A cofilin-specific siRNA sequence may be introduced into a host cell by various transfection methods. An effective cofilin-specific siRNA sequence may be introduced in a host cell for stable expression using techniques known in the art, for example, via shRNA vectors. The host cell may express the cofilin-specific siRNA sequence transiently or stably, preferably stably. The level of a cofilin protein in the host cell is knocked down, or reduced compared with that in a control cell. For example, the cofilin 1 protein level may be knocked down by at least about 5%, 10%, 20%, 30%, 40%, 50%, 60%, 70%, 80%, 90%, 95% or 99%, preferably at least about 10%, more preferably at least about 20%, most preferably at least about 30%.

The host cell may further comprise a nucleic acid sequence encoding a recombinant protein. The host cell may produce the recombinant protein. Preferably, the host cell produces more recombinant protein than its control cell. For example, the host cell may produce at least about 5%, 10%, 20%, 30%, 40%, 50%, 60%, 70%, 80%, 90%, 95% or 99%, preferably at least about 40%, more preferably at least about 50%, most preferably at least about 60%, more than the control cell. The host cell may have been transfected with a vector comprising the nucleic acid sequence encoding the recombinant protein.

The recombinant protein may be any suitable biopharmaceutical protein. It may be selected from the group consisting of monoclonal antibodies (e.g., anti-EGFR mAb, anti-VEGF mAb, Factor VIII, anti-IgE mAb, anti-CD11a mAb, interferon-$\beta$, anti-TNF$\alpha$ mAb, anti-CD52 mAb, anti-HER2 mAb, and anti-CD20 mAb), human secreted alkaline phosphatase (SEAP), tissue plasminogen activator (tPA), $\alpha$-glucosidase, laronidase, Ig-CTLA4 fusion, N-acetylgalactosamine-4-sulfatase, luteinizing hormone, erythropoietin, TNF$\alpha$ receptor fusion, Factor IX, follicle stimulating hormone, $\beta$-glucocerebrosidase, and deoxyribonuclease I. Preferably, the recombinant protein is human secreted alkaline phosphatase (SEAP) or tissue plasminogen activator (tPA).

RNAi efficiency and recombinant protein productivity may be assessed by various techniques known in the art. For example, cofilin 1 levels and GFP expression from the shRNA vectors may be monitored via western blotting. CHO-SEAP and CHO-tPA cells treated with a siRNA may be harvested and equivalent cell lysates resolved by SDS-PAGE and transferred to a Immobilon P membrane (Millipore). Samples may be probed with anti-cofilin, anti-actin, and anti-GFP antibodies (Sigma Aldrich) followed by alkaline phosphatase conjugated anti-mouse-IgG and anti-rabbit-IgG (Sigma Aldrich) and bands may be visualized using enhanced chemifluorescence substrate (GE Amersham Biosciences). Specific productivity levels may be assayed 72-96 hrs post-transfection in siRNA-treated or during culture of shRNA-expressing CHO-SEAP and CHO-tPA cells. SEAP production may be determined by incubation of heat-inactivated supernatant from treated cells with alkaline phosphatase yellow liquid substrate (Sigma Aldrich) and measuring absorbance at 405 nm. tPA production may be determined by incubation of heat-inactivated substrate from treated cells with tPA chromogenic substrate (Sigma Aldrich) and measuring absorbance at 405 nm. Human placental alkaline phosphatase standards (Sigma Aldrich) and recombinant human tPA standards (Oxford Biomedical Research) may be assayed in parallel to quantify specific productivity in units/cell/day.

The present invention also provides a method of producing a recombinant protein in the host cell of the present invention. The method comprises growing the host cell in a culture medium, wherein the host cell produces the recombinant protein. The host cell comprises a cofilin-specific siRNA sequence and a nucleic acid sequence encoding the recombinant protein, and produces less cofilin protein than a control cell. The method may further comprise isolating the recombinant protein from the host cell.

The host cells are preferably maintained under conditions suitable for producing a recombinant protein. Conditions suitable for commonly used host cells (e.g., CHO) to produce a recombinant protein are known in the art. For example, CHO cells may be cultured in IMDM media supplemented with 10% fetal bovine serum in a humidified incubator at 37° C. and 5% $CO_2$. The recombinant protein may be isolated from the host cell using conventional techniques known in the art. For example, the recombinant protein may be purified from the culture medium if secreted by the host cell, or extracted from the host cell if retained in the host cell. The resulting mixture may contain at least about 1%, 5%, 10%, 20%, 50%, 80% or 90% (by weight) of the recombinant protein.

In a method according to the present invention, the cofilin-specific small interfering RNA (siRNA) sequence is a nucleic acid sequence (RNA or DNA) capable of interfering with the expression of a cofilin gene and causing knockdown of the corresponding cofilin protein in a host cell comprising the nucleic acid sequence when compared with that in a control cell. The cofilin protein level may be knocked down by at least about 5%, 10%, 20%, 30%, 40%, 50%, 60%, 70%, 80%, 90%, 95% or 99%, preferably at least about 10%, more preferably at least about 20%, most preferably at least about 30%. The cofilin-specific siRNA sequence may target any sequence segment of a cofilin mRNA, preferably corresponding to a functional domain or region conserved among different mammalian species. For example, the siRNA sequence may comprise a sequence of 5'-CUAACUGCUACGAG-GAGGU-3' (S1) (SEQ ID NO:1) or 5'-GAAGAACAU-CAUCCUGGAG-3' (S2) (SEQ ID NO:2), targeting a cofilin 1 mRNA segment sequence corresponding to CAAACTGC-TACGAGGAGGT (SEQ ID NO: 3) or GAAGAACAT-CATCCTGGAG (SEQ ID NO: 4), respectively. A cofilin-specific siRNA sequence may be introduced into a host cell by various transfection methods. The host cell may express the cofilin-specific siRNA sequence transiently or stably, preferably stably. The host cell may be adherent or in suspension, preferably in suspension.

In a method according to the present invention, the host cell may produce the recombinant protein at least about 5%, 10%, 20%, 30%, 40%, 50%, 60%, 70%, 80%, 90%, 95% or 99%, preferably at least about 40%, more preferably at least about 50%, most preferably at least about 60%, than the untreated host cell. The host cell may have been transfected with a vector comprising a nucleic acid sequence encoding the recombinant protein. The recombinant protein may be selected from the group consisting of monoclonal antibodies (e.g., anti-EGFR mAb, anti-VEGF mAb, Factor VIII, anti-IgE mAb, anti-CD11a mAb, interferon-β, anti-TNFα mAb, anti-CD52 mAb, anti-HER2 mAb, and anti-CD20 mAb), human secreted alkaline phosphatase (SEAP), tissue plasminogen activator (tPA), α-glucosidase, laronidase, Ig-CTLA4 fusion, N-acetylgalactosamine-4-sulfatase, luteinizing hormone, erythropoietin, TNFα receptor fusion, Factor IX, follicle stimulating hormone, β-glucocerebrosidase, and deoxyribonuclease I. Preferably, the recombinant protein is human secreted alkaline phosphatase (SEAP) or tissue plasminogen activator (tPA).

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

EXAMPLE 1

Cofilin Expression in CHO Cells

The expression and subcellular localization of ADF/cofilin proteins in CHO-K1, CHO-SEAP and CHO-tPA cell lines was first examined. CHO-K1 cells were maintained as adherent cultures in Iscove's modified Dulbecco's medium (IMDM, HyClone, Logan, Utah) supplemented with 10% dialyzed fetal bovine serum (dFBS, Invitrogen, Carlsbad, Calif.). CHO-SEAP (Hayduk and Lee 2005) and CHO-tPA cells (ATCC CRL-9606) were maintained as adherent cultures in IMDM supplemented with 10% dFBS and 50 nM methotrexate (Calbiochem, San Diego, Calif.). To determine growth rates of adherent cells, CHO cells were plated in 6-well plates at $0.05 \times 10^6$ cells and viable cell counts, determined by trypan blue exclusion, were obtained every 2 days over a 10 day culture period. Average growth rates were calculated as previously described (Rasmussen et al. 1998).

Adherent CHO cells were resuspended at $1.0 \times 10^6$ cells/mL in cold phosphate buffered saline (PBS), lysed with 5×SDS sample buffer (50% glycerol, 5% SDS, 0.1% bromophenol blue in 0.25 M Tris), and heated at 95° C. for 5 min. Samples were subjected to electrophoresis on 12% T acrylamide SDS gels and transferred to Immobilon P membrane (Millipore, Bedford, Mass.). Samples were probed with anti-cofilin (1:1000, Sigma Aldrich), anti-ADF (1:500, Sigma Aldrich), and anti-β-actin (1:2000, Sigma Aldrich) followed by detection with alkaline phosphatase conjugated secondary antibodies (1:33,000, Sigma Aldrich). Western blots were developed using enhanced chemifluorescence substrate (GE Amersham Biosciences, Piscataway, N.J.) and imaged using a FLA-3000 Fujifilm scanner. Quantitative analysis was performed with ImageMaster 2D Platinum Software v5.0 (GE Amersham Biosciences).

CHO cells cultured in Lab-Tek II Chambers (Nalge Nunc International, Naperville, Ill.) were fixed with 4% paraformaldehyde (Electron Microscopy Supplies, Hatfield, Pa.) in PBS for 10 min at room temperature (RT) and quenched with 10 mg/mL bovine serum albumin (BSA) in PBS for 10 min at RT. Fixed cells were permeabilized with 0.1% TritonX-100 (Sigma Aldrich) and labeled first with either anti-ADF or anti-cofilin (Sigma Aldrich) followed by Alexa Fluor 555-conjuated secondary antibody (Invitrogen). The actin cytoskeleton was labeled with Alexa Fluor 647-phalloidin (Invitrogen) and cell nuclei were counterstained with DAPI (Invitrogen). Samples were imaged using a Zeiss LSM 510 NLO laser scanning microscope.

All three cell lines investigated expressed both ADF and cofilin, although expression of these proteins was higher in CHO-K1 cells than either recombinant CHO cell line (FIG. 1A). Both ADF and cofilin showed labeling throughout the cytoplasm in addition to nuclear labeling in CHO-K1 cells and cofilin localization was similar in recombinant CHO cell lines (FIG. 1B).

EXAMPLE 2

RNAi Design and Transfection

CHO-K1 cDNA was prepared using the SuperScript III CellsDirect cDNA synthesis kit (Invitrogen). Cofilin 1 cDNA was amplified from CHO-K1 cDNA using the PCR primers 5'-AAACATGGCCTCTGGTGTG-3' (SEQ ID NO: 5) and 5'-ACAAAGGCTTGCCCTCCAG-3' (SEQ ID NO: 6), designed against conserved regions between mouse (NM_007687) and rat (NM_017147) cofilin 1 sequences.

Two siRNAs (5'-CUAACUGCUACGAGGAGGU-3' (S1) (SEQ ID NO: 1) and 5'-GAAGAACAUCAUCCUGGAG-3' (S2) (SEQ ID NO: 2), which target cofilin 1 mRNA segment sequences corresponding to CAAACTGCTACGAGGAGGT (SEQ ID NO: 3) and GAAGAACATCATCCTGGAG (SEQ ID NO: 4), respectively) and a non-specific control siRNA (siRNA Universal Negative Control #1) were purchased from Sigma Aldrich (St. Louis, Mo.). Adherent CHO-SEAP and CHO-tPA cells were transfected with 90 nM siRNA using Lipofectamine 2000 (Invitrogen) either once or twice on two consecutive days. Suspension CHO-SEAP cells were transfected in 50 mL CultiFlask bioreactors (Sartorius Stedim Biotech, Göttingen, Germany) with 90 nM siRNA using Lipofectamine 2000. Transfected cells were first cultured for 48 hrs to allow for siRNA-mediated silencing and then incubated an additional 24-48 hrs before assaying for cofilin protein depletion and recombinant protein productivity.

shRNA vectors were generated by cloning siRNA coding sequences into the GeneSilencer pGSH1-GFP shRNA expression vector (Genlantis, San Diego, Calif.). Briefly, DNA oligos (Integrated DNA Technologies, Coralville, Iowa) were annealed and inserted into the linearized pGSH1-GFP vector. Oligos used for the pGSH1-GFP-S1 vector were 5'-GATCCGCTAA CTGCTACGAG GAGGTGAAGC TTGACCTCCT CGTAGCAGTT AGTTTTTTGG AAGC-3' (SEQ ID NO: 7) and 5'-GGCCGCTTCC AAAAAACAAA CTGCTACGAG GAGGTCAAGC TTCACCTCCT CGTAGCAGTT TGCG-3' (SEQ ID NO: 8). Oligos used for the pGSH1-GFP-S2 vector were 5'-GATCCGAAGA ACAT-CATCCT GGAGGAAGCT TGCTCCAGGA TGATGT-TCTT CTTTTTTGGA AGC-3' (SEQ ID NO: 9) and 5'-GGC-CGCTTCC AAAAAAGAAG AACATCATCC TGGAGCAAGC TTCCTCCAGG ATGATGTTCT TCG-3' (SEQ ID NO: 10). An empty pGSH1-GFP vector was used as a negative control. Adherent CHO-SEAP and CHO-tPA cells were co-transfected with shRNA plasmid vectors and pcDNA3.1/Zeo (Invitrogen) with 4 μg total plasmid DNA using Lipofectamine 2000. Positive cells were selected by 500 μg/mL zeocin (Invitrogen).

EXAMPLE 3

Transient Silencing of Cofilin Using siRNA

A partial cofilin 1 cDNA sequence was cloned and sequenced from CHO-K1 cells and used to design siRNAs targeting two different positions. These siRNA sequences were transfected individually (S1 or S2) or co-transfected together (S12) into recombinant CHO cell lines. As described in Examples 1 and 2, adherent CHO-SEAP and CHO-tPA cells were maintained, and transfected with cofilin-specific (S1, S2, S12) or non-specific (NC) control siRNAs and assayed for effects on recombinant protein production 72-96 hrs post-transfection.

Activity assays were used to monitor protein production from the supernatant of adherent and suspension cells. SEAP production was measured by dispensing 50 µL of CHO-SEAP culture supernatant, after dilution into IMDM and heat-inactivation for 30 min at 65° C., into a 96-well plate and adding 50 µL of alkaline phosphatase yellow liquid substrate (Sigma Aldrich). tPA production was measured by dispensing 8 µl of CHO-tPA culture supernatant into a 96-well plate and adding 72 µl of Tris buffer (30 mM Tris, 30 mM imidazole, 130 mM NaCl, pH 8.4) and 20 µl, of tPA chromogenic substrate (Sigma Aldrich). The activity assays were monitored by measuring absorbance at 405 nm at 37° C. using a Molecular Devices VersaMax microplate reader. Human placental alkaline phosphatase (Type XXIV, Sigma Aldrich) and recombinant human tPA (Oxford Biomedical Research, Oxford, Mich.) standards were assayed in parallel and used to construct standard curves. Specific productivity was calculated by normalizing by time and cell number.

Figure 2:
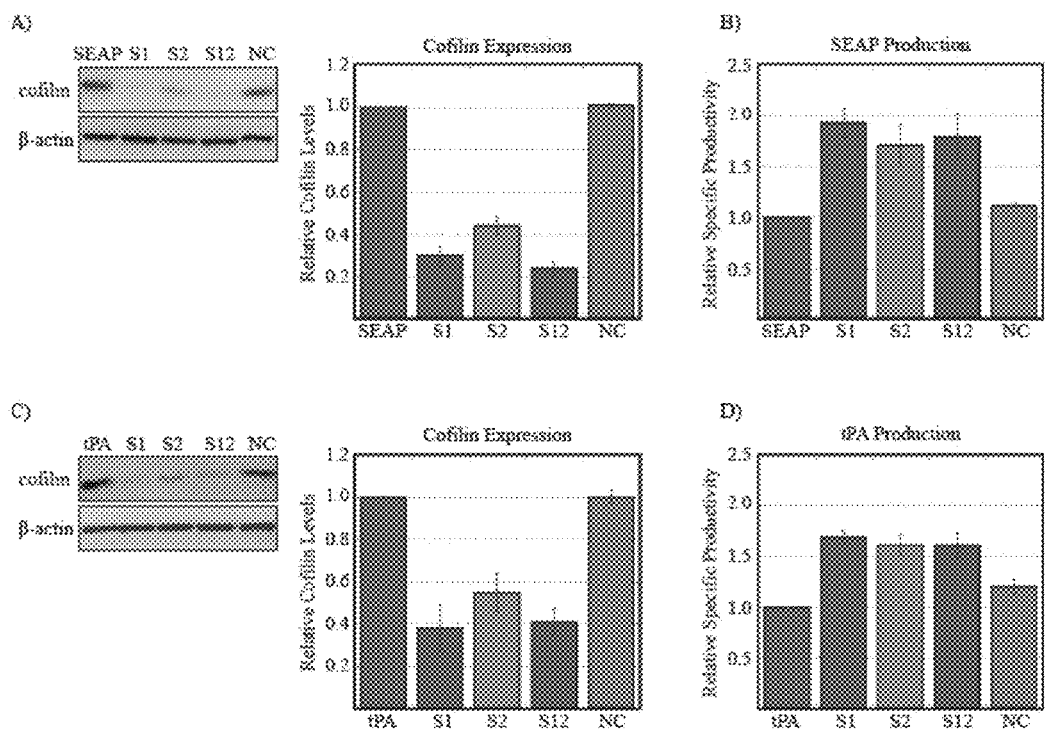
FIG. 2 shows transient cofilin reduction in CHO cells by siRNA: relative cofilin expression in (A) CHO-SEAP and (C) CHO-tPA cells analyzed by western blotting, in which β-actin was used as a loading control, and relative specific productivity of (B) CHO-SEAP and (D) CHO-tPA cells. CHO cells were treated with cofilin-specific (S1, S2, S12) or non-specific control (NC) siRNA. Samples were assayed 72-96 hrs post-transfection and are normalized to CHO-SEAP or CHO-tPA. The mean and standard error of the mean of four independent experiments are shown.

In CHO-SEAP cells, a 57% (S2) to 77% (S12) reduction in cofilin expression (FIG. 2A) and a 71% (S2) to 93% (S1) increase in specific SEAP productivity (FIG. 2B) was observed in cells treated with cofilin-specific siRNA compared to a non-specific control siRNA. CHO-tPA cells transfected with an siRNA targeting cofilin showed a 45% (S2) to 62% (S1) reduction in cofilin expression (FIG. 2C) and a 41% (S12) to 49% (S1) enhancement of specific tPA productivity (FIG. 2D) compared to a non-specific siRNA.

Figure 3:
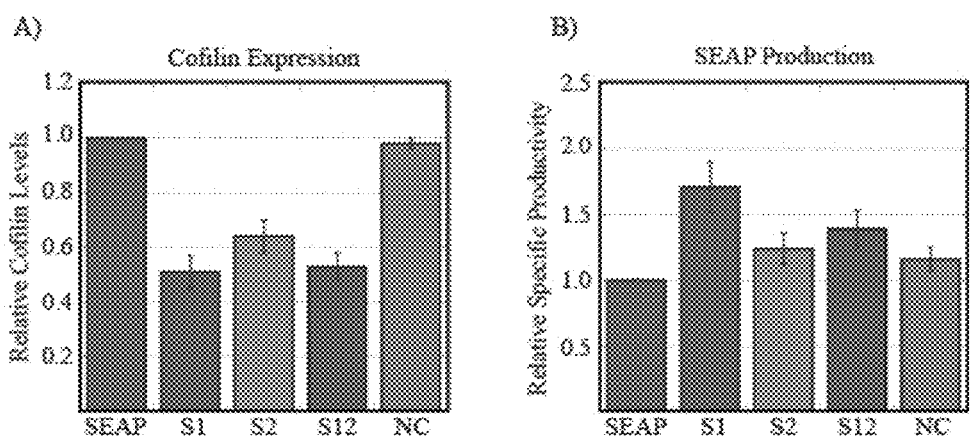
FIG. 3 shows cofilin reduction in suspension CHO cells by siRNA: (A) relative cofilin expression in suspension CHO-SEAP cells analyzed by western blotting, and (B) relative specific productivity of suspension CHO-SEAP cells. Suspension cells were treated with cofilin-specific (S1, S2, S12) or non-specific control (NC) siRNA. Samples were assayed 72-96 hrs post-transfection and normalized to CHO-SEAP. The mean and standard error of the mean of six independent experiments are shown.

To examine the effects of cofilin reduction in suspension cells, adherent CHO-SEAP cells were adapted into suspension culture in 125 mL shake flasks. Suspension CHO-SEAP cells were transfected with cofilin-specific (S1, S2, S12) or non-specific (NC) siRNAs and recombinant protein production was assayed 72-96 hrs post-transfection. A 34% (S2) to 47% (S1) reduction in cofilin expression (FIG. 3A) and an 8% (S2) to 55% (S1) increase in specific productivity (FIG. 3B) was observed in suspension cells treated with cofilin-specific siRNA.

EXAMPLE 4

Stable Reduction of Cofilin by shRNA

To generate cell lines with long term cofilin depletion, siRNA sequences were cloned into GeneSilencer shRNA expression vectors. These plasmids allow for the continual production of shRNAs, which are processed inside the cell into siRNAs, and also express GFP to allow for identification of transfected cells. As described in Examples 1-3, the cells were maintained and the activity assays were used to monitor protein production.

Figure 4:
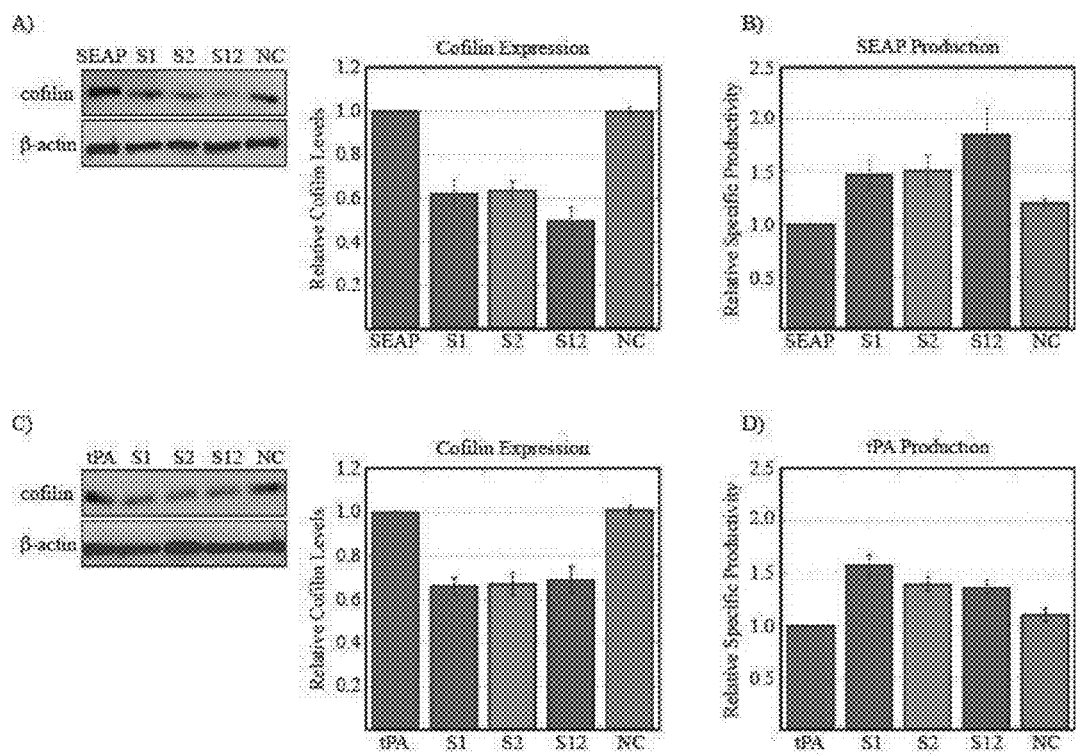
FIG. 4 shows stable cofilin reduction in CHO cells by shRNA: relative cofilin expression in (A) CHO-SEAP and (C) CHO-tPA cells analyzed by western blotting, in which β-actin was used as a loading control, and relative specific productivity of (B) CHO-SEAP and (D) CHO-tPA cells. CHO cells expressed cofilin-specific shRNA (S1, S2, S12) or control (NC) vectors. Samples were normalized to CHO-SEAP or CHO-tPA. The mean and standard error of the mean of five independent experiments are shown.

Adherent CHO cells were co-transfected with individual cofilin shRNA plasmids (S1 and S2), a combination of cofilin shRNA plasmids (S12), or an empty shRNA vector (NC) along with a vector conferring zeocin resistance for selection of stable cell lines. CHO-SEAP cells expressing cofilin-specific shRNA vectors showed a 36% (S2) to 50% (S12) reduction in cofilin levels (FIG. 4A) and a 48% (S1) to 85% (S12) increase in specific SEAP productivity (FIG. 4B) compared to cells expressing an empty shRNA vector. CHO-tPA cells expressing cofilin-specific shRNA vectors showed a 32% (S12) to 35% (S1) decrease in cofilin expression (FIG. 4C) and a 26% (S12) to 47% (S1) enhancement of specific tPA productivity (FIG. 4D) compared to control cells.

The effect of cofilin reduction on cell growth was also examined. Recombinant CHO cells expressing both cofilin-specific and control shRNA vectors showed similar, although slightly slower growth rates compared to the parental CHO-SEAP and CHO-tPA cell lines (Table I). Viability for all CHO cell lines remained above 90% during the culture period.

TABLE I

Average growth rates (doubling time) of CHO cell lines expressing shRNA vectors.

| Cell Line | Doubling Time (hrs) | Cell Line | Doubling Time (hrs) |
| --- | --- | --- | --- |
| CHO-SEAP | 27.6 ± 1.9 | CHO-tPA | 25.7 ± 0.9 |
| CHO-SEAP-S1 | 29.1 ± 2.2 | CHO-tPA-S1 | 26.1 ± 0.5 |
| CHO-SEAP-S2 | 28.1 ± 3.3 | CHO-tPA-S2 | 28.1 ± 2.5 |
| CHO-SEAP-S12 | 30.4 ± 2.5 | CHO-tPA-S12 | 27.0 ± 1.2 |
| CHO-SEAP-GSH1 | 29.1 ± 1.8 | CHO-tPA-GSH1 | 27.3 ± 0.4 |

EXAMPLE 5

Reduced Cofilin Expression Alters the Actin Cytoskeleton

Figure 5:
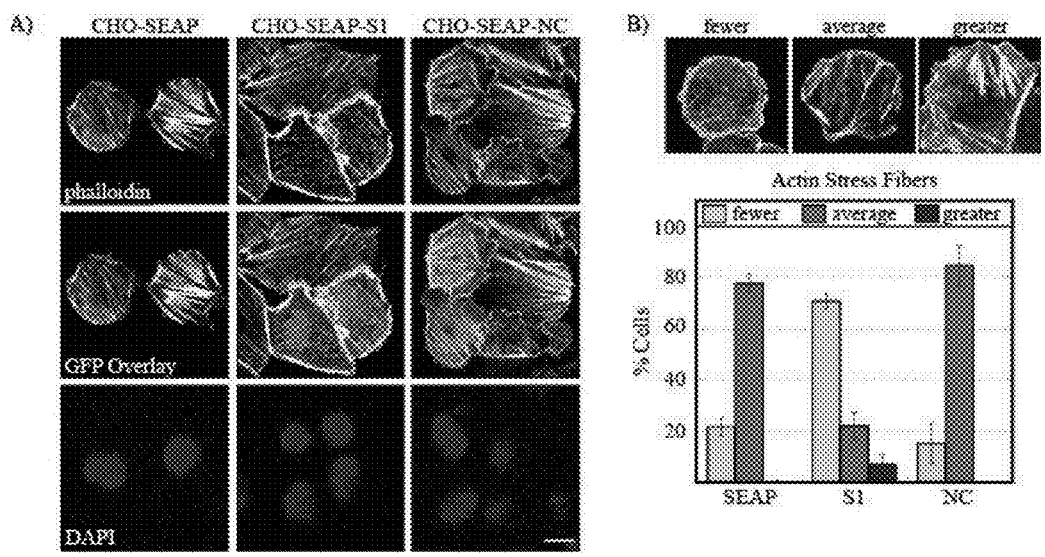
FIG. 5 shows actin cytoskeleton changes in CHO cells expressing cofilin-specific shRNA. (A) CHO-SEAP cells expressing cofilin-specific shRNA (CHO-SEAP-S1) or an empty vector (CHO-SEAP-NC) were stained with phalloidin (white) (upper panels). Cells expressing shRNA vectors also express GFP (green) (middle panels). Nuclei were counterstained with DAPI (lower panels). The scale bar represents 10 μM. (B) Representative images of CHO cells stained with phalloidin that show fewer, average, or greater number of actin filaments are shown (white) (upper panels). Average percentage of cells that showed fewer, average, or greater number of actin filaments compared to CHO-SEAP cells (lower panel). For each cell type, 43-100 cells were evaluated over five independent experiments. The mean and standard error of the mean are shown.

The effect of cofilin reduction on cytoskeleton structure was examined in CHO-SEAP cells expressing an individual shRNA vector (CHO-SEAP-S1) or an empty shRNA vector control (CHO-SEAP-NC). As described in Examples 1-4, cells were maintained, and labeled with phalloidin to visualize actin filaments and cells expressing vectors were identified by GFP expression. Cofilin depletion by shRNA decreased the number of actin stress fibers in CHO-SEAP-S1 cells compared to control cells (FIG. 5A). Cells were subdivided into three categories and scored visually: cells showing average F-actin labeling, cells showing fewer actin filaments, and cells showing greater labeling of F-actin stress fibers (FIG. 5B). Approximately 80% of CHO-SEAP and CHO-SEAP-NC cells showed average F-actin labeling, whereas only 22% of CHO-SEAP-S1 cells displayed normal actin filament structure. More than 70% of CHO-SEAP-S1 cells showed fewer actin filaments and less than 10% showed more prominent labeling of actin filaments.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

REFERENCES

Alete D E, Racher A J, Birch J R, Stansfield S H, James D C, Smales C M. 2005. Proteomic analysis of enriched microsomal fractions from GS-NS0 murine myeloma cells with varying secreted recombinant monoclonal antibody productivities. Proteomics 5(18):4689-704.

Andrianantoandro E, Pollard T D. 2006. Mechanism of actin filament turnover by severing and nucleation at different concentrations of ADF/cofilin. Mol Cell 24(1):13-23.

Bernstein B W, Bamburg J R. 2010. ADF/Cofilin: a functional node in cell biology. Trends Cell Biol 20:187-95.

Beuger V, Künkele K P, Koll H, Gärtner A, Bähner M, Burtscher H, Klein C. Short-hairpin-RNA-mediated silencing of fucosyltransferase 8 in Chinese-hamster ovary cells for the production of antibodies with enhanced antibody immune effector function. Biotechnology and Applied Biochemistry (2009) 53, 31-37.

Carlage T, Hincapie M, Zang L, Lyubarskaya Y, Madden H, Mhatre R, Hancock W S. 2009. Proteomic profiling of a high-producing Chinese hamster ovary cell culture. Anal Chem 81(17):7357-62.

Chan A Y, Bailly M, Zebda N, Segall J E, Condeelis J S. 2000. Role of cofilin in epidermal growth factor-stimulated actin polymerization and lamellipod protrusion. J Cell Biol 148 (3):531-42.

Chua B T, Volbracht C, Tan K O, Li R, Yu V C, Li P. 2003. Mitochondrial translocation of cofilin is an early step in apoptosis induction. Nat Cell Biol 5(12):1083-9.

Cost G J, Freyvert Y, Vafiadis A, Santiago Y, Miller J C, Rebar E, Collingwood T N, Snowden A, Gregory P D. BAK and BAX deletion using zinc-finger nucleases yields apoptosis-resistant CHO cells. Biotechnology and Bioengineering (2010) 105, 330-340.

Dawe H R, Minamide L S, Bamburg J R, Cramer L P. 2003. ADF/cofilin controls cell polarity during fibroblast migration. Curr Biol 13(3):252-7.

Dinnis D M, James D C. 2005. Engineering mammalian cell factories for improved recombinant monoclonal antibody production: lessons from nature? Biotechnol Bioeng 91(2):180-9.

Elbashir S M, Harborth J, Lendeckel W, Yalcin A, Weber K, Tuschl T. Duplexes of 21-nucleotide RNAs mediate RNA interference in cultured mammalian cells. Nature (2001) 411, 494-498.

Grzanka D, Marszalek A, Gagat M, Izdebska M, Gackowska L, Grzanka A. 2010. Doxorubicin-induced F-actin reorganization in cofilin-1 (nonmuscle) down-regulated CHO AA8 cells. Folia Histochem Cytobiol 48(3):377-86.

Han L, Stope M B, de Jesus M L, Oude Weernink P A, Urban M, Wieland T, Rosskopf D, Mizuno K, Jakobs K H, Schmidt M. 2007. Direct stimulation of receptor-controlled phospholipase D1 by phospho-cofilin. Embo J 26(19):4189-202.

Hayduk E J, Lee K H. 2005. Cytochalasin D can improve heterologous protein productivity in adherent Chinese hamster ovary cells. Biotechnol Bioeng 90(3):354-64.

Hong W W, Wu S C. A novel RNA silencing vector to improve antigen expression and stability in Chinese hamster ovary cells. Vaccine (2007) 25, 4103-4111.

Hotulainen P, Paunola E, Vartiainen M K, Lappalainen P. 2005. Actin-depolymerizing factor and cofilin-1 play overlapping roles in promoting rapid F-actin depolymerization in mammalian nonmuscle cells. Mol Biol Cell 16(2):649-64.

Ichetovkin I, Grant W, Condeelis J. 2002. Cofilin produces newly polymerized actin filaments that are preferred for dendritic nucleation by the Arp2/3 complex. Curr Biol 12(1):79-84.

Kandasamy M K, McKinney E C, Meagher R B. 2010. Differential sublocalization of actin variants within the nucleus. Cytoskeleton 67(11):729-43.

Kantardjieff A, Jacob N M, Yee J C, Epstein E, Kok Y J, Philp R, Betenbaugh M, Hu W S. 2010. Transcriptome and proteome analysis of Chinese hamster ovary cells under low temperature and butyrate treatment. J Biotechnol 145(2): 143-59.

Klamt F, Zdanov S, Levine R L, Pariser A, Zhang Y, Zhang B, Yu L R, Veenstra T D, Shacter E. 2009. Oxidant-induced apoptosis is mediated by oxidation of the actin-regulatory protein cofilin. Nat Cell Biol 11(10):1241-6.

Kumar N, Gammell P, Meleady P, Henry M, Clynes M. 2008. Differential protein expression following low temperature culture of suspension CHO-K1 cells. BMC Biotechnol 8:42.

Kuystermans D, Dunn M J, Al-Rubeai M. 2010. A proteomic study of cMyc improvement of CHO culture. BMC Biotechnol 10:25.

Lee K H, Meuer S C, Samstag Y. 2000. Cofilin: a missing link between T cell co-stimulation and rearrangement of the actin cytoskeleton. Eur J Immunol 30(3):892-9.

Lim S F, Chuan K H, Liu S, Loh S O, Chung B Y, Ong C C, Song Z. RNAi suppression of Bax and Bak enhances viability in fed-batch cultures of CHO cells. Metabolic Engineering (2006) 8, 509-522.

Meleady P, Henry M, Gammell P, Doolan P, Sinacore M, Melville M, Francullo L, Leonard M, Charlebois T, Clynes M. 2008. Proteomic profiling of CHO cells with enhanced rhBMP-2 productivity following co-expression of PACEsol. Proteomics 8(13):2611-24.

Mori K, Kuni-Kamochi R, Yamane-Ohnuki N, Wakitani M, Yamano K, Imai H, Kanda Y, Niwa R, Iida S, Uchida K and others. 2004. Engineering Chinese hamster ovary cells to maximize effector function of produced antibodies using FUT8 siRNA. Biotechnol Bioeng 88(7):901-8.

Ngantung F A, Miller P G, Brushett F R, Tang G L, Wang D L 2006. RNA interference of sialidase improves glycoprotein sialic acid content consistency. Biotechnol Bioeng 95(1):106-19.

Nishita M, Tomizawa C, Yamamoto M, Horita Y, Ohashi K, Mizuno K. 2005. Spatial and temporal regulation of cofilin activity by LIM kinase and Slingshot is critical for directional cell migration. J Cell Biol 171(2):349-59.

Pascoe D E, Arnott D, Papoutsakis E T, Miller W M, Andersen D C. 2007. Proteome analysis of antibody-producing CHO cell lines with different metabolic profiles. Biotechnol Bioeng 98(2):391-410.

Rasmussen B, Davis R, Thomas J, Reddy P. 1998. Isolation, characterization and recombinant protein expression in Veggie-CHO: A serum-free CHO host cell line. Cytotechnology 28(1-3):31-42.

Sidani M, Wessels D, Mouneimne G, Ghosh M, Goswami S, Sarmiento C, Wang W, Kuhl S, El-Sibai M, Backer J M and others. 2007. Cofilin determines the migration behavior and turning frequency of metastatic cancer cells. J Cell Biol 179(4):777-91.

Smales C M, Dinnis D M, Stansfield S H, Alete D, Sage E A, Birch J R, Racher A J, Marshall C T, James D C. 2004. Comparative proteomic analysis of GS-NS0 murine myeloma cell lines with varying recombinant monoclonal antibody production rate. Biotechnol Bioeng 88(4):474-88.

Sung Y H, Lee J S, Park S H, Koo J, Lee G M. Influence of co-down-regulation of caspase-3 and caspase-7 by siRNAs on sodium butyrate-induced apoptotic cell death of Chinese hamster ovary cells producing thrombopoietin. Metabolic Engineering (2007) 9, 452-464.

Tsai C H, Chiu S J, Liu C C, Sheu T J, Hsieh C H, Keng P C, Lee Y J. 2009. Regulated expression of cofilin and the consequent regulation of p27(kip1) are essential for G(1) phase progression. Cell Cycle 8(15):2365-74.

Vartiainen M K, Mustonen T, Mattila P K, Ojala P J, Thesleff I, Partanen J, Lappalainen P. 2002. The three mouse actin-depolymerizing factor/cofilins evolved to fulfill cell-type-specific requirements for actin dynamics. Mol Biol Cell 13(1):183-94.

von Blume J, Duran J M, Forlanelli E, Alleaume A M, Egorov M, Polishchuk R, Molina H, Malhotra V. 2009. Actin remodeling by ADF/cofilin is required for cargo sorting at the trans-Golgi network. J Cell Biol 187(7):1055-69.

Wu S C. 2009. RNA interference technology to improve recombinant protein production in Chinese hamster ovary cells. Biotechnol Adv 27(4):417-22.

Wurm F M. 2004. Production of recombinant protein therapeutics in cultivated mammalian cells. Nat Biotechnol 22(11):1393-8.

Zhang M, Koskie K, Ross J S, Kayser K J, Caple M V. 2010. Enhancing glycoprotein sialylation by targeted gene silencing in mammalian cells. Biotechnol Bioeng 105(6): 1094-105.

What is claimed:

1. A host cell comprising a cofilin-specific small interfering RNA (siRNA) sequence and a nucleic acid sequence encoding a recombinant protein, wherein the host cell produces less cofilin protein and more recombinant protein than a control cell, and wherein the control cell does not comprise the cofilin-specific small interfering RNA (siRNA) sequence.

2. The host cell of claim 1, wherein the cofilin-specific siRNA sequence comprises SEQ ID NO: 1 or SEQ ID NO: 2.

3. The host cell of claim 1, wherein the host cell expresses the cofilin-specific siRNA sequence.

4. The host cell of claim 1, wherein the recombinant protein is tissue plasminogen activator (tPA).

5. The host cell of claim 1, wherein the host cell is a CHO cell or a derivative thereof.

6. The host cell of claim 1, wherein the host cell produces at least 10% cofilin protein less than the control cell.

7. The host cell of claim 1, wherein the host cell produces at least 40% recombinant protein more than the control cell.

8. A method of producing a recombinant protein by a host cell comprising a cofilin-specific small interfering RNA (siRNA) sequence and a nucleic acid sequence encoding the recombinant protein, comprising growing the host cell in a culture medium, wherein the host cell produces less cofilin protein and more recombinant protein than a control cell, and wherein the control cell does not comprise the cofilin-specific small interfering RNA (siRNA) sequence.

9. The method of claim 8, further comprising isolating the recombinant protein from the host cell.

10. The method of claim 8, wherein the cofilin-specific siRNA sequence comprises SEQ ID NO: 1 or SEQ ID NO: 2.

11. The method of claim 8, wherein the host cell expresses the cofilin-specific siRNA sequence.

12. The method of claim 8, wherein the host cell produces at least 10% cofilin protein less than the control cell.

13. The method of claim 8, wherein the host cell produces at least 40% recombinant protein more than the control cell.

14. The method of claim 8, wherein the recombinant protein is tissue plasminogen activator (tPA).

15. The method of claim 8, wherein the host cell is a CHO cell or a derivative thereof.

* * * * *

SEQUENCE LISTING

<160> NUMBER OF SEQ ID NOS: 10

<210> SEQ ID NO 1
<211> LENGTH: 19
<212> TYPE: RNA
<213> ORGANISM: Artificial Sequence
<220> FEATURE:
<223> OTHER INFORMATION: synthetic sequence

<400> SEQUENCE: 1
cuaacugcua cgaggaggu                                              19

<210> SEQ ID NO 2
<211> LENGTH: 19
<212> TYPE: RNA
<213> ORGANISM: Artificial Sequence
<220> FEATURE:
<223> OTHER INFORMATION: synthetic sequence

<400> SEQUENCE: 2
gaagaacauc auccuggag                                              19

<210> SEQ ID NO 3
<211> LENGTH: 19
<212> TYPE: DNA
<213> ORGANISM: Cricetulus griseus

<400> SEQUENCE: 3
caaactgcta cgaggaggt                                              19

<210> SEQ ID NO 4
<211> LENGTH: 19
<212> TYPE: DNA
<213> ORGANISM: Cricetulus griseus

<400> SEQUENCE: 4
gaagaacatc atcctggag                                              19

<210> SEQ ID NO 5
<211> LENGTH: 19
<212> TYPE: DNA
<213> ORGANISM: Artificial Sequence
<220> FEATURE:
<223> OTHER INFORMATION: Synthetic sequence

<400> SEQUENCE: 5
aaacatggcc tctggtgtg                                              19

<210> SEQ ID NO 6
<211> LENGTH: 19
<212> TYPE: DNA
<213> ORGANISM: Artificial Sequence
<220> FEATURE:
<223> OTHER INFORMATION: Synthetic sequence

<400> SEQUENCE: 6

```
acaaaggctt gccctccag                                              19

<210> SEQ ID NO 7
<211> LENGTH: 64
<212> TYPE: DNA
<213> ORGANISM: Artificial Sequence
<220> FEATURE:
<223> OTHER INFORMATION: Synthetic sequence

<400> SEQUENCE: 7
gatccgctaa ctgctacgag gaggtgaagc ttgacctcct cgtagcagtt agtttttgg   60 aagc                                                              64

<210> SEQ ID NO 8
<211> LENGTH: 64
<212> TYPE: DNA
<213> ORGANISM: Artificial Sequence
<220> FEATURE:
<223> OTHER INFORMATION: Synthetic sequence

<400> SEQUENCE: 8
ggccgcttcc aaaaacaaa ctgctacgag gaggtcaagc ttcacctcct cgtagcagtt   60
tgcg                                                              64

<210> SEQ ID NO 9
<211> LENGTH: 63
<212> TYPE: DNA
<213> ORGANISM: Artificial Sequence
<220> FEATURE:
<223> OTHER INFORMATION: Synthetic sequence

<400> SEQUENCE: 9
gatccgaaga acatcatcct ggaggaagct tgctccagga tgatgttctt cttttttgga   60
agc                                                               63

<210> SEQ ID NO 10
<211> LENGTH: 63
<212> TYPE: DNA
<213> ORGANISM: Artificial Sequence
<220> FEATURE:
<223> OTHER INFORMATION: Synthetic sequence

<400> SEQUENCE: 10
ggccgcttcc aaaaagaag aacatcatcc tggagcaagc ttcctccagg atgatgttct   60
tcg                                                               63
```